United States Patent
Su

(10) Patent No.: US 9,216,931 B1
(45) Date of Patent: Dec. 22, 2015

(54) PROCESS FOR RECOVERING OLEFINS IN POLYOLEFIN PLANTS

(71) Applicant: Paul Su, Saratoga, CA (US)

(72) Inventor: Paul Su, Saratoga, CA (US)

(73) Assignee: Membrane Technology and Research, Inc., Newark, CA (US)

( * ) Notice: Subject to any disclaimer, the term of this patent is extended or adjusted under 35 U.S.C. 154(b) by 0 days.

(21) Appl. No.: 14/722,738

(22) Filed: May 27, 2015

Related U.S. Application Data

(63) Continuation-in-part of application No. 14/486,382, filed on Sep. 15, 2014, now Pat. No. 9,073,808.

(51) Int. Cl.
  *C07C 7/144* (2006.01)
  *C07C 7/09* (2006.01)
  *C07C 7/00* (2006.01)

(52) U.S. Cl.
  CPC . *C07C 7/005* (2013.01); *C07C 7/09* (2013.01); *C07C 7/144* (2013.01)

(58) Field of Classification Search
  None
  See application file for complete search history.

(56) References Cited

U.S. PATENT DOCUMENTS

| | | |
|---|---|---|
| 4,623,704 A | 11/1986 | Dembicki et al. |
| 5,089,033 A | 2/1992 | Wijmans |
| 5,199,962 A | 4/1993 | Wijmans |
| 5,769,927 A | 6/1998 | Gottschlich et al. |
| 6,271,319 B1 | 8/2001 | Baker et al. |
| 7,479,227 B2 * | 1/2009 | Da Costa et al. ............. 210/640 |
| 2007/0232847 A1 * | 10/2007 | Minhas et al. ................ 585/818 |
| 2011/0077446 A1 * | 3/2011 | Shanbhag et al. ............ 585/818 |

OTHER PUBLICATIONS

Handbook of Petrochemicals and Processes, G.M. Wells, Gower Publishing, 1995.

* cited by examiner

*Primary Examiner* — Tam M Nguyen
(74) *Attorney, Agent, or Firm* — Timothy A. Hott; Janet Farrant

(57) ABSTRACT

A process for recovering unreacted olefin in a polyolefin manufacturing process comprising the treatment of a purge bin vent gas. The process involves cooling and condensing the vent gas (purge stream), which contains at least an olefin, a paraffin, and hydrogen, to produce a liquid condensate and an uncondensed (residual) gas stream. Both streams are then passed through membrane separation steps. The membrane separation of the uncondensed gas stream results in a residue stream containing mostly nitrogen and/or paraffin and a permeate stream enriched in either $C_{2+}$ hydrocarbons or olefin, depending on the type of separation. The permeate from this step is recirculated within the process prior to the condensation step. The membrane separation of the condensate results in a residue stream containing paraffin and a permeate stream enriched in olefin, which may be recycled to the polymerization reactor.

15 Claims, 9 Drawing Sheets

PROCESS FOR RECOVERING OLEFINS IN POLYOLEFIN PLANTS

CROSS-REFERENCE TO RELATED APPLICATIONS

This application is a continuation-in-part of U.S. application Ser. No. 14/486,382 filed Sep. 15, 2014, now U.S. Pat. No. 9,073,808, the disclosure of which is hereby incorporated herein by reference in its entirety.

FIELD OF THE INVENTION

The invention relates to a process for recovering olefins in a polyolefin manufacturing process. More specifically, the invention relates to treating a purge bin vent gas stream using gas separation membranes for recovering unreacted olefin and selectively purging paraffin from the polymerization process.

BACKGROUND OF THE INVENTION

Polyethylene (PE) and polypropylene (PP) are two of the most demanded polymers in the world. Together, these polymers make up half of the volume of plastic produced worldwide.

During polyolefin production, a small portion of the olefin feedstock is lost through raw material purification, chemical reaction, and product purification and finishing. In particular, paraffin that enters with the olefin feedstock must be removed to prevent its build up in the reactor loop, and olefin is lost when this paraffin is purged from the loop. This results in an annual loss of $1 million to $3 million per year for a typical polyolefin plant. The development of a more efficient way to prevent the loss of olefin monomer in the feedstock has been an on-going process for those in the petrochemical field.

In polyolefin manufacturing, a feedstock containing olefin monomer, catalysts, and other agents is introduced into a high-pressure polymerization reactor. During the reaction, a raw polymer product is produced. The raw product contains polyolefin, significant amounts of unreacted olefin, and small amounts of solvents, catalysts, stabilizers, other hydrocarbons or any other materials, depending on the manufacturing process used. To remove the volatile contaminants dissolved in the raw product, it is passed to large bins, where nitrogen is used to purge them out. The vent gas from this step contains nitrogen, unreacted olefin monomer, unwanted analogue paraffins that entered with the olefin feedstock, and other process-specific materials. In the past, this vent gas was sent for flaring, resulting in a waste of unreacted olefin.

Various process and techniques have been proposed for mitigating the loss of unreacted olefin in the vent stream.

U.S. Pat. No. 4,623,704, to Dembicki et al. (Dow Chemical Company), discloses a process for treating a polymerization vent gas with a membrane. The vent stream is compressed and then cooled and condensed. Cooled gas and liquid are sent to a liquid/gas separator. After separation, the gas stream is sent through a series of membrane separation steps, which produce a permeate stream enriched in ethylene. The recovered ethylene is recycled to the polymerization process.

Co-owned U.S. Pat. Nos. 5,089,033 and 5,199,962, to Wijmans (Membrane Technology and Research, Inc.), disclose processes for recovering a condensable component in a gas stream that would otherwise be discharged into the atmosphere. The processes involve a condensation step and a membrane separation step. In one embodiment, the gas stream is compressed and cooled to carry out the condensation step. Uncondensed gas is then passed across a membrane that is selectively permeable to the condensable component.

Co-owned U.S. Pat. No. 6,271,319, to Baker et al. (Membrane Technology and Research, Inc.), discloses a process for treating the uncondensed gas stream using a gas separation membrane that is permeable for propylene over propane. A permeate stream enriched in olefin is withdrawn and recycled to the reactor inlet.

These patents, and other prior art technologies, have mainly focused on condensing the vent stream and recovering unreacted olefin from the resulting uncondensed gas produced from the condensation step. However, little is taught on recovering unreacted olefins from the condensed liquid stream.

Co-owned U.S. Pat. No. 5,369,927, to Gottschlich et al. (Membrane Technology and Research, Inc.), discloses a process for treating a purge vent stream from a polymer manufacturing operation. The purge vent stream contains an unreacted olefin monomer and nitrogen. The purge vent stream is initially treated in a condensation step. The uncondensed gas is then passed to a membrane separation step, where the membrane is organic-selective, meaning that the membrane is selective for unreacted monomer over other gases. The liquid condensate is directed to a flashing step. The flashing step produces a liquid product stream enriched in monomer and a flash gas that is recirculated in the process.

Although it is known that the permeate stream from the membrane separation of the uncondensed gas stream, such as that disclosed in U.S. Pat. No. 6,271,319, above, is enriched in olefin, the condensed liquid stream still contains unwanted contaminants, such as paraffin and dissolved nitrogen. Thus, there remains a need to further treat purge bin vent streams to recover unreacted olefin.

SUMMARY OF THE INVENTION

Accordingly, the present invention relates to a process for recovering olefins by treating a purge bin vent stream in a polyolefin manufacturing plant. The purge bin vent stream is referred to herein as a "purge stream." During treatment, the purge stream is condensed and separated, producing a liquid condensate stream and an uncondensed gas stream. Both of these streams contain unreacted olefin along with other components, such as paraffin, nitrogen, and light gases. To recover the unreacted olefin, both streams are treated by membrane separation steps. From treating the uncondensed gas stream, the olefin recovered is recycled back into the process upstream of the condensation step. Recovered unreacted olefin from treating the liquid condensate may be sent in a recycle loop to the polymerization reactor for use as feedstock.

Therefore, in a basic embodiment, the process of the invention includes the following steps:
(a) passing a purge stream to a compressor to produce a compressed stream;
(b) partially condensing the compressed stream, including cooling and separating the compressed stream into a condensed liquid condensate enriched in olefin and paraffin and an uncondensed (residual) gas stream depleted in olefin and paraffin relative to the compressed stream;
(c) separating the condensed liquid condensate from step (b) using a first membrane to produce a first olefin-enriched permeate stream and a first paraffin-enriched residue stream;
(d) separating the uncondensed gas stream from step (b) using a second membrane to produce a first hydrocarbon-enriched permeate stream and a first hydrocarbon-depleted residue stream; and (e) returning the first hydrocarbon-enriched permeate stream upstream of the compressor.

The purge stream of step (a) comprises at least an olefin, an analagous paraffin and nitrogen. In certain embodiments, the olefin is ethylene or propylene. In other embodiments, the olefin is butylene. The purge stream may also comprise other light gases, including water vapor, methane, nitrogen, and hydrogen. The purge stream may also contain multiple sets of olefins and analogous paraffins, for example, ethane/ethylene and propane/propylene.

The goal of steps (a) and (h) is to bring the purge stream to a pressure/temperature condition beyond the dewpoint of the olefin to be recovered, so that a portion of the olefin will condense out of the gas stream. Thus, the separation of the compressed stream creates a liquid condensate and an uncondensed (residual) gas stream. The condensate is enriched in olefin and paraffin and the uncondensed gas stream depleted in olefin and paraffin relative to the purge stream.

The condensation step usually involves chilling and compression. Compressing the has raises the dewpoint temperature, so a combination of compression and chilling is generally preferred. Occasionally, however, the purge process, or other upstream treatments, may be such that the purge stream is already at high pressure. In this case, chilling alone may suffice to induce condensation, and the compression step may be dispensed with.

In step (c), the liquid condensate from condensation step (b) is treated in a membrane separation step, which may be carried out under pervaporation or vapor permeation conditions. The membrane in this step is selective for olefin over paraffin. The membrane separation of step (c) thus results in a first permeate stream enriched in olefin and a first residue stream enriched in paraffin.

In certain embodiments, the permeate stream enriched in olefin from step (c) is directed as a coolant stream to the condensation train prior to being sent to the polymerization reactor.

Membranes for use in step (c) of the process of the invention may comprise any material suitable for preferentially permeating olefin over paraffin. In certain embodiments, the membrane preferably exhibits an olefin permeance of at least 400 gpu.

Step (c) may take the form of a single membrane separation operation or of multiple sub-operations, depending on the feed composition, membrane properties, and desired results.

In step (d), the uncondensed gas stream from condensation step (b) is passed as a feed stream and treated in a second membrane separation step. The membranes in step (d) are selectively permeable to $C_{2+}$ hydrocarbons over other gases. A permeate stream enriched in hydrocarbons and a residue stream depleted in hydrocarbons are withdrawn from the membrane. The residue stream may be of sufficient nitrogen purity to be reused in the purge bin.

In other embodiments, the membrane in step (d) is selective for olefin over paraffin, thus resulting in a second permeate stream enriched in olefin and a second residue stream depleted in olefin, but enriched in paraffin. Thus, in certain aspects, the membranes in step (d) may comprise any material suitable for preferentially permeating olefins over Paraffins and nitrogen/other gases.

In step (e), the permeate stream from step (d) is recycled upstream of the compressor of step (a).

In a further embodiment, the process described above may be used to further separate the uncondensed gas stream. The hydrocarbon-depleted residue stream, or in some aspects, the paraffin-enriched residue stream, from step (d) is passed through an additional membrane separation step to produce a permeate stream enriched in light gases and paraffin and a residue stream enriched in nitrogen. The membrane used in this step may be any material suitable for selectively permeating $C_{2+}$ hydrocarbons over other gases. The permeate stream is typically flared while the nitrogen in the residue stream may be recycled for use in the purge bin. Thus, in certain embodiments, the process comprises the steps (a)-(e), above, and the additional step of:

(f) separating the first hydrocarbon-depleted residue stream from step (d) using a third membrane to produce a second hydrocarbon-enriched permeate stream and a second hydrocarbon-depleted residue stream.

If the membrane in step (d) is selective for olefin over paraffin, the process comprises steps (a)-(e), above, and the additional step of:

(f) separating the second paraffin-enriched residue stream from step (d) using a thud membrane to produce a hydrocarbon-enriched permeate stream and a hydrocarbon-depleted residue stream.

In certain embodiments, the process described above may also be used to further treat the liquid condensate stream by incorporating a further membrane separation step. The first paraffin-enriched residue stream from step (c) is passed through an additional membrane separation step to produce a second (or third) permeate stream enriched in olefin and a second (or third) residue stream enriched in paraffin. The second enriched olefin permeate stream may then be recycled upstream of the compression step. Thus, in certain embodiments, the process comprises the steps (a)-(f), above, and the additional steps of:

(g) separating the first paraffin-enriched residue stream using a fourth membrane to produce a second, or in some aspects a third, olefin-enriched permeate stream and a second paraffin-enriched residue stream; and (h) returning the second (or third) olefin-enriched permeate stream upstream of the compressor.

If the membrane separation of the condensate stream is to be carried out in the vapor phase, then the condensate stream must first be vaporized, such as by increasing the temperature or decreasing the pressure. In this particular embodiment, therefore, the process comprises the steps of (a) passing a purge stream from a polymerization reactor purge bin to a compressor to produce a compressed stream;

(b) partially condensing the compressed stream, including cooling and separating the compressed stream into a condensed liquid stream enriched in olefin and paraffin and an overhead gas stream depleted in olefin and paraffin;

(c) vaporizing the condensed liquid stream to create a vapor feed stream;

(d) separating the vapor feed stream from step (c) using a first membrane to produce a first olefin-enriched permeate stream and a first paraffin-enriched residue stream;

(e) separating the overhead gas stream from step (b) using a second membrane to produce a first hydrocarbon-enriched permeate stream and a first hydrocarbon-depleted stream; and (f) returning the first hydrocarbon-enriched permeate stream upstream of the compressor.

In certain embodiments, the process comprises the steps (a)-(f), above, and the additional step of:

(g) passing the first hydrocarbon-depleted stream from step (c) as a feed stream across a third membrane to produce a second hydrocarbon-enriched permeate stream and a second hydrocarbon-depleted stream.

In certain embodiments, the process comprises the steps (a)-(g), above, and the additional steps of
- (h) passing the first paraffin-enriched residue stream from step (d) as a feed stream across a fourth membrane to produce a second olefin-enriched permeate stream and a second paraffin-enriched residue stream; and
- (i) returning the second olefin-enriched permeate stream upstream of the compressor in step (a);

In other embodiments, the membrane in step (e) may comprise any material suitable for preferentially permeating olefins over paraffins and nitrogen/other gases. This step results in a second permeate stream enriched in olefin and a second residue stream enriched in paraffin.

If the membrane in step (e) is selective for olefin over paraffin, the process comprises steps (a)-(f), above, and the additional step of
- (g) separating the second paraffin-enriched residue stream from step (e) using a third membrane to produce a hydrocarbon-enriched permeate stream and a hydrocarbon-depleted residue stream.

In certain embodiments, the process comprises the steps (a)-(g), above, and the additional steps of:
- (h) passing the first paraffin-enriched residue stream from step (d) as a feed stream across a fourth membrane to produce a third olefin-enriched permeate stream and a third paraffin-enriched residue stream; and
- (i) returning the third olefin-enriched permeate stream upstream of the compressor in step (a);

In further embodiments, the purge stream may contain relatively high concentrations of hydrogen in addition to olefins and paraffins. In this case, hydrogen may be recovered from the uncondensed gas stream using a hydrogen-selective membrane. Thus, in certain embodiments, step (d), above, is preceded by this hydrogen separation step. In these embodiments, the process comprises the steps of:
- (a) passing the feed gas stream to a compressor to produce a compressed stream;
- (b) partially condensing the compressed stream, including cooling and separating the compressed stream into a condensed liquid condensate enriched in olefin and paraffin and an uncondensed (residual) gas stream depleted in olefin and paraffin relative to the compressed stream;
- (c) separating the condensed liquid condensate from step (b) using a first membrane to produce a first olefin-enriched permeate stream and a first paraffin-enriched residue stream;
- (d) separating the uncondensed gas stream from step (h) using a second membrane to produce a hydrogen-enriched permeate stream and a hydrogen-depleted residue stream;
- (e) separating the hydrogen-depleted residue from step (d) using a third membrane to produce a hydrocarbon-enriched permeate stream and a hydrocarbon-depleted residue stream; and
- (f) returning the hydrocarbon-enriched residue stream upstream of the compressor.

In some embodiments, the process above further comprises the steps of:
- (g) separating the first paraffin-enriched residue stream using a fourth membrane to produce a second olefin-enriched permeate stream and a second paraffin-enriched residue stream; and
- (h) returning the second olefin-enriched permeate stream upstream of the compressor.

Similar to the processes discussed above, in embodiments where the condensate stream needs to be vaporized, a hydrogen recovery step may be included. In these particular embodiments, the process comprises the steps of:
- (a) passing said gas stream to a compressor to produce a compressed stream;
- (b) partially condensing the compressed stream, including cooling and separating the compressed stream into a condensed liquid stream enriched in olefin and paraffin and an overhead gas stream depleted in olefin and paraffin;
- (c) vaporizing the condensed liquid stream to create a vapor feed stream;
- (d) the vapor feed stream from step (c) using a first membrane to produce a first olefin-enriched permeate stream and a first paraffin-enriched residue stream;
- (e) separating the overhead gas stream from step (b) using a second membrane to produce a hydrogen-enriched permeate stream and a hydrocarbon-depleted residue stream;
- (f) separating the hydrogen-depleted residue stream from step (e) using a third membrane to produce a hydrocarbon-enriched permeate stream and a hydrocarbon-depleted residue stream; and
- (g) returning the hydrocarbon-enriched residue stream upstream of the compressor, In some aspects, the above embodiment may further comprise the steps of:
- (h) passing the first paraffin-enriched residue stream from step (d) as a feed stream across a fourth membrane to produce a second olefin-enriched permeate stream and a second paraffin-enriched residue stream; and
- (i) returning the second olefin-enriched permeate stream upstream of the compressor.

In yet another embodiment, the invention relates to an olefin recovery process comprising a reactor loop incorporating the reactor itself, the polymer separation equipment, including a purge bin and a purge stream recovery step, including membrane separation units containing olefin-selective membranes and hydrocarbon-selective membranes.

In an alternative embodiment, it may be desirable to treat only the overhead gas stream to separate olefin from paraffin and nitrogen. The overhead gas stream from the condensation step, described as in step (b) above, is separated using a first membrane to produce a first olefin-enriched permeate stream and a first paraffin-enriched stream. The first olefin-enriched permeate stream is then returned upstream of the compressor. The first paraffin-enriched stream is passed as a feed stream across a second membrane to produce a hydrocarbon-enriched permeate stream and a hydrocarbon-depleted stream. The condensed stream from the condensation step is collected and may be used for any desired purpose.

It is to be understood that the above summary and the following detailed description are intended to explain and illustrate the invention without restricting it in scope.

DETAILED DESCRIPTION OF THE INVENTION

The term "olefin" as used herein means a member of the family of unsaturated hydrocarbons having a carbon-carbon double bond of the series $C_nH_{2n}$, including members in which at least one halogen atom has been substituted for one of the hydrogen atoms.

The term "$C_{2+}$ hydrocarbon" means a hydrocarbon having at least two carbon atoms.

The invention relates to an improved process for recovering unreacted olefin in a polyolefin manufacturing process. The process also provides for selectively purging paraffin from the polymerization reactor loop. By a reactor loop, we mean a configuration in which at least a part of the purge stream from the polymerization reactor is recirculated directly or indirectly to the reactor. The process can be applied to any olefin polymerization loop in which olefin is fed to the reactor, and in which olefin and paraffin are present in the purge steam from the reaction loop.

Figure 1:
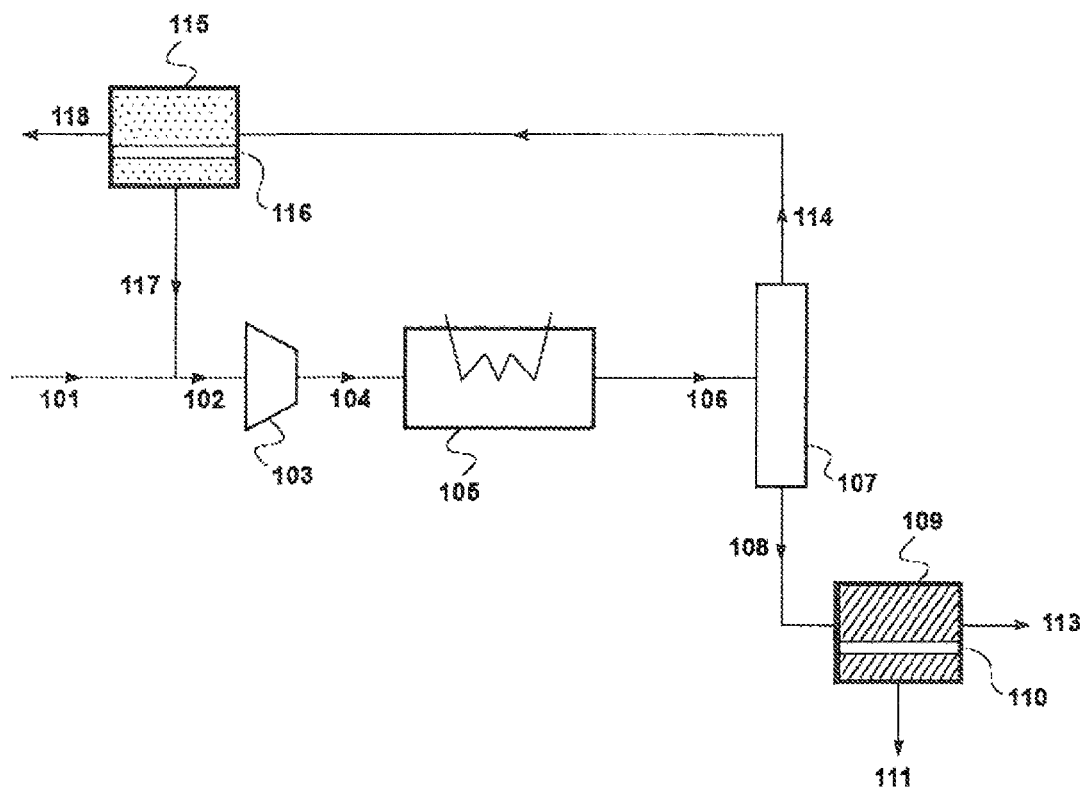
FIG. 1 is a schematic drawing showing a purge stream recovery process comprising two membrane separation steps according to a basic embodiment of the invention.

A basic process according to the invention is shown in FIG. 1.

It will be appreciated by those of skill in the art that FIG. 1 and the other figures showing process schemes herein are very simple block diagrams, intended to make clear the key unit operations of the embodiment processes of the invention, and that actual process trains may include many additional steps of standard type, such as heating, chilling, compressing, condensing, pumping, various types of separation and/or fractionation, as well as monitoring of pressures, temperatures, flows, and the like. It will also be appreciated by those of skill in the art that the details of the unit operations may differ from process to process.

The purge stream is generated inside a purge bin, where nitrogen is used to purge unreacted monomers from polymer powders produced by the polymerization process. It will be apparent to those of skill in the art that the above are general, non-limiting descriptions of preferred polymerization reaction techniques that are well known. More information about these and other specific arrangements is available in petrochemical engineering reference books, for example, *Handbook of Petrochemicals and Processes*, G. M. Wells, Gower Publishing, 1995. It will further be apparent that the reactor operating conditions and functioning are not critical to pressures, temperatures, flows, and the like. It will also be appreciated by those of skill in the art that the details of the unit operations may differ from process to process.

A basic embodiment of the purge stream recovery process is shown in FIG. 1.

A purge stream, 101, from a polyolefin polymerization process is combined with recycled unreacted olefin, stream 117, to produce gas mixture stream 102. The purge stream typically contains at least nitrogen, unreacted olefin monomer and paraffin that was introduced with the raw olefin feedstock. The ratio of olefin to paraffin in the stream may be as much as 5:1, 6:1 or even 7:1 or more. If this stream were to be purged from the polymerization plant without further treatment, then as many as five, six, or seven volumes of olefin would be lost for every volume of paraffin that is purged.

Gas mixture stream 102 is routed to compression step, 103, the goal of which is to compress the stream to a pressure which the gas mixture may be partially condensed in the subsequent process steps. The compression step may be carried out using compression equipment of any convenient type, and may be performed in one stage or in a multistage compression train, depending on the degree of compression needed. It is preferred that the pressure to which stream 102 is raised be no more than about 35 bara, and more preferably no more than about 30 bara.

The stream emerging from compression step 103 is compressed stream 104. This stream is sent to a condensation step, 105. The condensation step includes cooling of stream 104 to below the olefin dewpoint temperature, such that a major portion of the olefin is condensed, followed by separation of the resulting liquid and gas phases. Cooling may be performed in any manner, and in one or more sub-steps, including, but not limited to, simple air or water aftercooling of the compressor outlet gases, heat exchange against other on-site process streams, chilling by external refrigerants, and any combinations of these. Preferably, this step should cool stream 104 to a temperature no lower than −40° C., and yet more preferably to no colder than about −35° C.

The liquid and gas phases that are formed by compression and cooling are separated by conventional means in a knockout drum or the like, 107, to yield condensed liquid stream, 108, and uncondensed gas stream, 114. The condensed liquid stream 108 typically comprises 80 mol %, 90 mol %, or more olefin and paraffin.

Stream 108 is then sent as a feed stream to a membrane separation step, 109. Any membrane with suitable performance properties may be used in this step. The membrane may take the form of a homogeneous film, an integral asymmetric membrane, a multilayer composite membrane, a membrane incorporating a gel or a liquid layer or particulates, or any other form known in the art.

The membrane or membranes to be used in step 109 are made of any material suitable for selectively permeating olefin over paraffin. Preferably, the membranes provide propylene/propane selectivity of at least 5 and propylene flux of 400 gpu under favorable conditions. For ethylene/ethane separation, the preferred selectivity of the membrane is 5 and the preferred ethylene flux is 400 gpu.

These membranes are preferably inorganic membranes. Inorganic membranes with olefin/paraffin separating properties are very finely porous and act as very fine sieves that separate on the basis of polarity difference. Inorganic membranes are characterized by good temperature and chemical resistance. More preferably, the inorganic membranes are zeolite membranes. Such membranes include, but are not limited to, zeolite-based membranes that are crystalline oxides consisting of silicon, aluminum, and other cations, such as sodium and potassium coated on ceramic or other types of support structures.

In some embodiments, membranes for separating olefin and paraffins include polymeric membranes. Typically, these membranes have a selective layer made from a glassy polymer. Representative examples of these membranes include, but are not limited to, poly(phenylene oxide) (PPO), polyimides, perflourinated polyimides, Hyflon® AD, and Cytop®.

In other embodiments, the membranes used in step 109 may include facilitated transport membranes. These contain a liquid that itself contains, for example, free silver ions that react selectively and reversibly with unsaturated hydrocarbons, to selectively carry olefin (propylene) across the membrane.

The membranes may be manufactured as flat sheets or as hollow fibers and housed in any convenient module form, including spiral-wound modules, tubular modules, plate-and-frame modules, and potted hollow-fiber modules. The making of all these types of membranes and modules is well-known in the art.

The membrane separation steps disclosed herein may be carried out using a single membrane module or a bank of membrane modules or an array of modules. A single unit or stage containing on or a bank of membrane modules is adequate for many applications. If either the residue or permeate stream, or both, requires further olefin removal, it may be passed to a second bank of membrane modules for a second processing step. Such multi-stage or multi-step processes, and variants thereof, will be familiar to those of skill in the art, who will appreciate that the membrane separation step may be configured in many possible ways, including single-stage, multistage, multistep, or more complicated arrays of two or more units, in serial or cascade arrangements.

The membrane separation steps disclosed herein can be operated by any mechanism that provides a driving force for transmembrane permeation. Most commonly, this driving force is provided by maintaining a pressure difference between the feed and permeate sides, or by sweeping the permeate side continuously with a gas that dilutes the permeating species, both of which techniques are well known in the membrane separation arts.

The membrane separation step, 109, may occur under vapor permeation or pervaporation conditions. By "pervaporation conditions" we mean that the feed is heated to elevate its vapor pressure but maintained at a sufficiently high pressure to prevent evaporation on the feed side of the membrane. The permeate side is maintained at a pressure substantially below the vapor pressure of the feed so vapor will permeate the membrane. If membrane separation step 109 occurs under pervaporation conditions, liquid stream 108 is first heated and then flows to and across the feed side of membrane 110. The low pressure permeate vapor, enriched in the more permeable component, may optionally be cooled and condensed (not shown) or may be compressed and condensed or a combination of the two.

If membrane separation step 109 occurs under vapor permeation conditions, liquid stream 108 is heated and vaporized before flowing across the feed side of membrane 110.

Heating of the liquid stream is shown in further detail in FIG. 3, which is described in more detail below. Liquid stream 108a is heated by direct heater 112 of any convenient type to produce a heated liquid stream 108b, if under pervaporation conditions, or a vaporized stream 108b, if under vapor permeation conditions.

Referring back to FIG. 1, under either condition, a residue stream, 113, that is depleted in olefin relative to stream 108, is withdrawn from the feed side of the membrane. The membrane separation step reduces the olefin content of this stream, preferably to the point that the ratio of olefin to paraffin in the stream is reduced to about 1:1, and more preferably below 1:1. This stream may be purged flout the process with comparatively little loss of olefin.

The permeate stream, 111, is enriched in olefin compared with the membrane feed. Optionally, in certain embodiments, this stream may be used as a coolant for heat recovery at various locations within the process to minimize refrigerant energy usage. For example, permeate stream 111 may be used as a coolant in the heat-exchange/condensation step 105, emerging as warmed permeate stream.

Alternatively, if membrane separation step 109 takes place under pervaporation conditions, it may be more beneficial to cool and condense stream 111 to provide or augment the driving force for the pervaporation step.

Permeate stream 111 represents a substantial source of recovered olefin, preferably containing a chemical grade olefin, having an olefin content of at least 90%. In a preferred embodiment, permeate stream 111 is returned as feedstock to the polymerization reactor. In this case, the permeate stream most preferably contains a polymer grade olefin, having an olefin content of about 99% or above, such as 99.5%.

Uncondensed gas stream, 114, is sent as a feed stream to a second membrane separation step, 115. Prior to this, it may be desirable to heat stream 114 to recover heat and/or to have optimal operating temperatures. Heating of stream 114 may be accomplished by in any way, for example by heat exchange against other on-site process stream or with steam. In FIG. 1, the heat exchange may occur between hot compressed gas stream 104 and cold uncondensed gas stream 114.

The membrane separation step is carried out in a membrane unit containing membrane(s), 116, that are selectively permeable to $C_{2+}$ hydrocarbons over other gases. The membranes preferably have a selectivity for hydrocarbons over other gases of at least about 5, more preferably greater than 10, and a hydrocarbon permeance of at least about 400 gpu.

Any membrane with suitable performance properties may be used in the membrane separation step. Typically, these membranes are polymeric and are preferably have a selective layer that comprises a rubbery or elastomeric polymer. Representative preferred membranes include, but are not limited to, nitrile rubber, neoprene, polydimethylsiloxane (silicone rubber), chlorosulfonated polyethylene, polysilicone-carbonate copolymers, and fluoroelastomers. Silicone rubber is the most preferred material for use in this step.

A driving force for transmembrane permeation is provided by a pressure difference between the feed and permeate sides of the membrane. If the uncondensed gas after the condensation step, remains at high pressure, such as above 5 bara, then this is usually adequate to carry out the membrane separation step without additional compression.

Stream 114 flows across the fed side of membrane 116. A residue stream, 118, that is depleted in hydrocarbons relative to stream 114, is withdrawn from the feed side of the membrane. This stream typically contains a high percentage of nitrogen and may be reused in the purge bin, or further treated to separate nitrogen from other gases to reuse in the polymerization process. The permeate stream, 117, is enriched in hydrocarbons compared with the membrane feed. Stream 11 is then recycled and combined with purge stream 101 upstream of compression step 103.

Figure 2:
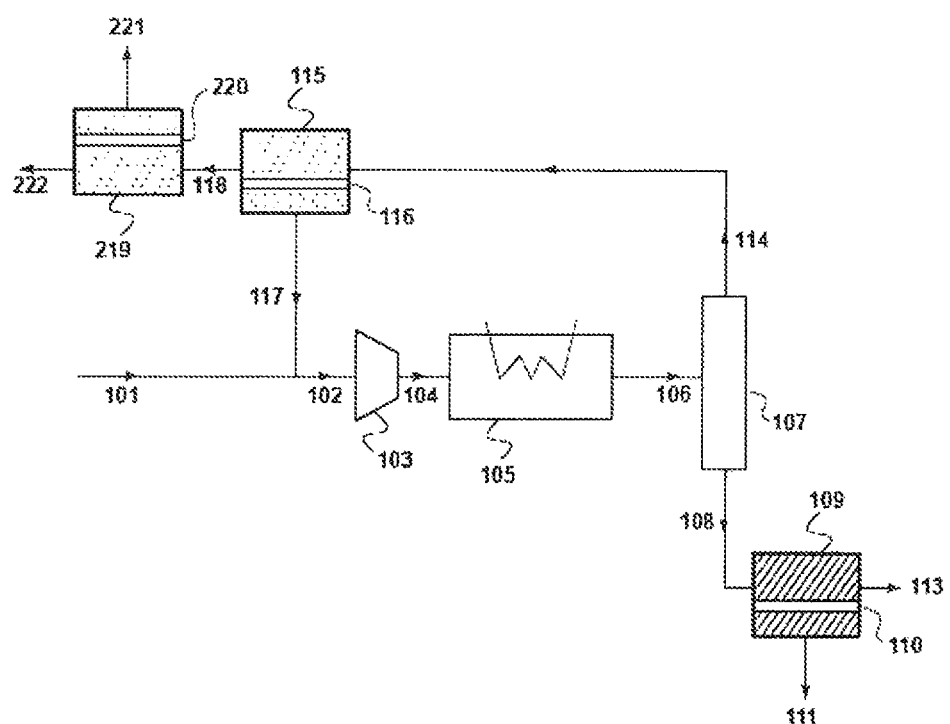
FIG. 2 is a schematic drawing showing a process flow scheme for a variant of the process of FIG. 1, comprising a third membrane separation step.

Another embodiment of the purge stream recovery process is shown in FIG. 2. This embodiment is similar to that of FIG.

1 in that the condensed liquid stream 108 and uncondensed gas stream 114 undergo membrane separation.

Depleted hydrocarbon residue stream 118 is further treated by a third membrane separation step, 219. Stream 118 acts as a feed stream and passes across membrane 220 that is selectively permeable to $C_{2+}$ hydrocarbons over other gases. The residue stream, 222, contains nitrogen, which may be recycled back to the polyolefin purification process. The permeate stream, 221, is enriched in $C_{1+}$ hydrocarbons and other light gases, which may be sent off to flare or any other suitable destination.

For membrane separation step 219 the preferred membrane materials are similar to the polymeric membranes used in membrane separation step 115, described above.

Figure 3:
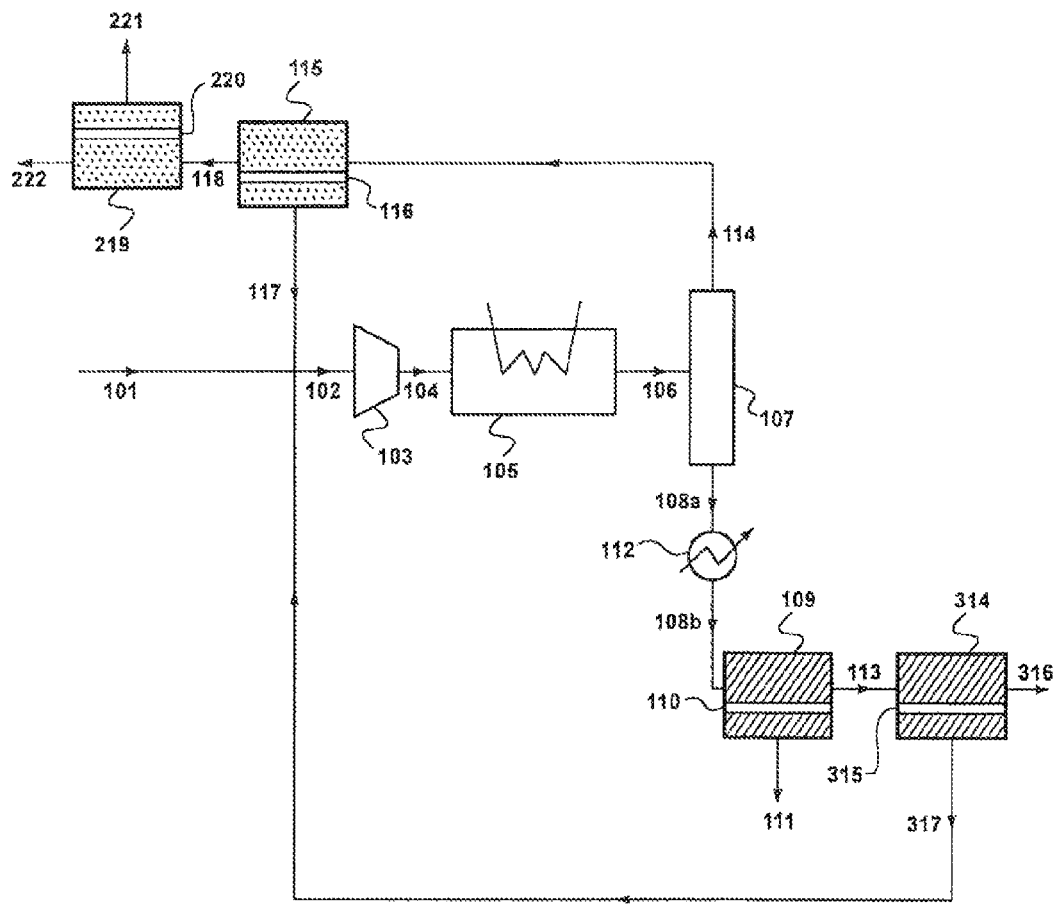
FIG. 3 is a schematic drawing showing a process flow scheme for a variant of the process of FIG. 2, comprising a fourth membrane separation step.

Another embodiment of the purge stream recovery process is shown in FIG. 3. This embodiment is similar to that of FIG. 2 in that the condensed liquid stream 108, the uncondensed gas stream 114, and residue stream 118 undergo membrane separation.

Residue stream, 113, that is depleted in olefin relative to stream 108, is further treated by a fourth membrane separation step, 314. Stream 113 is passed as a feed stream across membrane 315 that is selectively permeable to olefin over paraffin. The residue stream, 316, contains a major part/most of the paraffin in the purge stream 101 and is purged from the process. The permeate stream, 317, is enriched in olefin and is recycled upstream of compression step 103. The the embodiments of FIGS. 3, 4, 6 and 7, with a suitably high recycle stream 317 or 617, the paraffin content of stream 111 or 512 may be low enough that it can be sent back the polymerization reactor.

Preferred membranes for membrane separation step 314 are inorganic membranes, similar to those used in membrane separation step 109, described above.

Figure 4:
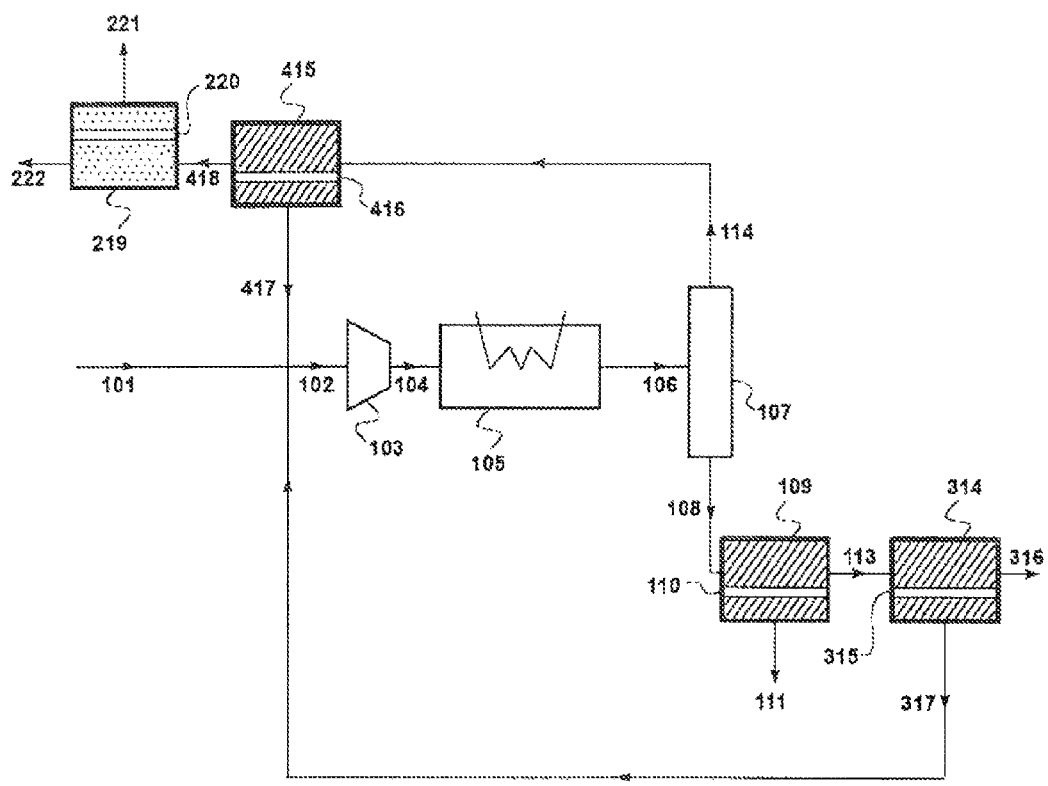
FIG. 4 is a schematic drawing showing a process flow scheme for a variant of the process of FIG. 3, in which the membrane of the second separation step comprises of a different material than that of the membrane in the second separation step in FIG. 3.

Another embodiment of the purge stream recovery process is shown in FIG. 4. This embodiment is similar to that of FIG. 3 in that condensed liquid stream 108, first residue stream 113, and uncondensed gas stream 114 undergo membrane separation.

Uncondensed gas stream, 114, is sent as a feed stream to membrane separation step 415. This step is carried out in a membrane unit containing membrane(s), 416, that are selectively permeable to olefin over paraffin and nitrogen/other gases. The membranes preferably are inorganic membranes, similar to those used in membrane separation steps 109 and 314.

Stream 114 flows across the feed side of membrane 416. A residue stream, 418, that is depleted in olefin relative to stream 416, is withdrawn from the feed side of the membrane. While depleted in olefin, this stream comprises paraffin, nitrogen, and other light gases. Residue stream 418 is then sent to membrane separation step 219 for further treatment as described above. The permeate stream, 417, is enriched in olefin compared with the membrane feed. Stream 417 is recycled and combined with purge stream 101 upstream of compression step 103.

Figure 5:
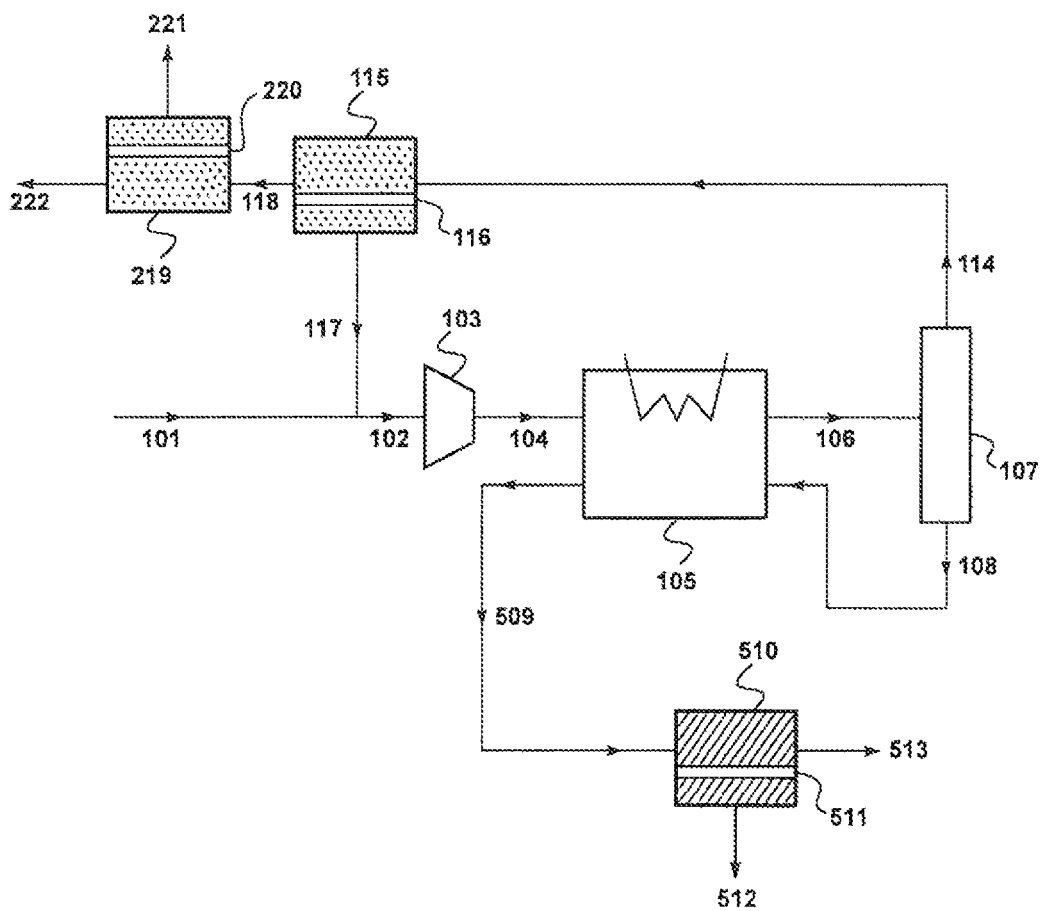
FIG. 5 is a schematic drawing showing a process flow scheme for a variant of the process of FIG. 4, in which the membrane separation step of the condensate is carried out in the vapor phase.

An alternative process configuration to recover unreacted olefin in the purge stream is shown in FIG. 5. This embodiment is similar to that of FIG. 2, except that the condensed liquid stream, 108, is vaporized and the membrane separation step, 510, is carried out in the gas phase. Unless stated otherwise, options and preferences for the various unit operations and streams entering and leaving them in this figure are the same as in the embodiments of FIG. 1-4.

Stream 108 is passed through a heating step where the condensed liquid is vaporized into gas to form stream 509. Heating may be carried out in any way, for example by heat exchange with a suitable hot stream if available on-site, or with steam. In FIG. 5, the heat exchange occurs between hot compressed gas stream 104 and the cold liquid condensate stream 108. In the alternative, stream 108 could be vaporized using a lower temperature heat source by reducing the pressure on the stream by means of a valve or the like.

Vapor stream 509 is then sent as a feed stream to a membrane separation step, 510. This step is carried out in a membrane unit containing membranes, 511, that are selectively permeable to olefin over paraffin. Preferred membranes for this step are similar to those used in membrane separation step 109 in FIG. 1.

Stream 509 flows across the feed side of membrane 511. A residue stream, 513, that is depleted in olefins, but enriched in paraffin relative to stream 509, is withdrawn from the feed side of the membrane and exits the process as a purge gas. Permeate stream 512 is enriched in olefin compared with the membrane feed and may be recycled back to the polymerization reactor or sent for further processing.

Figure 6:
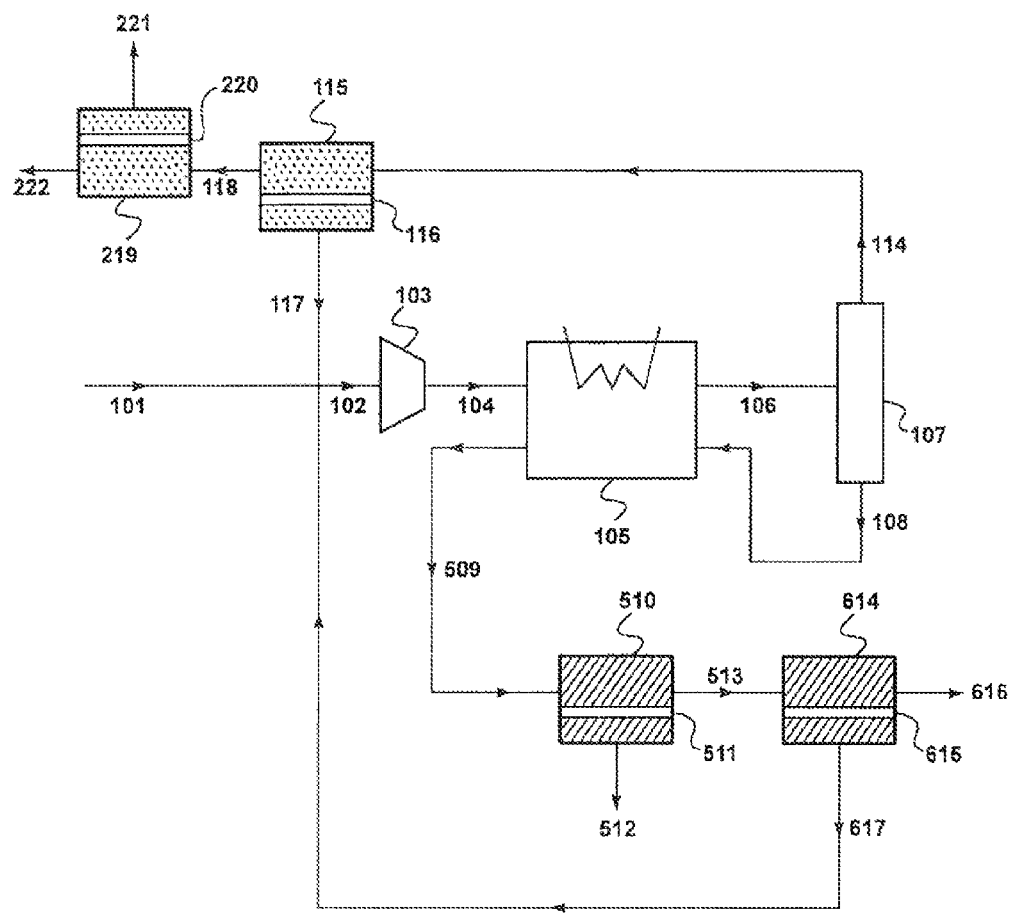
FIG. 6 is a schematic drawing showing a process flow scheme for a variant of the process of FIG. 5, comprising a fourth membrane separation step.

Another embodiment of the purge stream recovery process is shown in FIG. 6. This embodiment is similar to that of FIG. 5, but residue stream 513 is further treated with a fourth membrane step.

Residue stream, 513, depleted in olefin relative to stream 509, is further treated by membrane separation step 614. Residue stream 513 is passed as a feed stream across membrane 615 that is selectively permeable to olefin over paraffin. Preferably, these membranes are the same as those used in membrane separation step 510. The residue stream, 616, contains paraffin that is purged from the process. The permeate stream, 617, is enriched in olefin and is recycled upstream of compression step 103.

Figure 7:
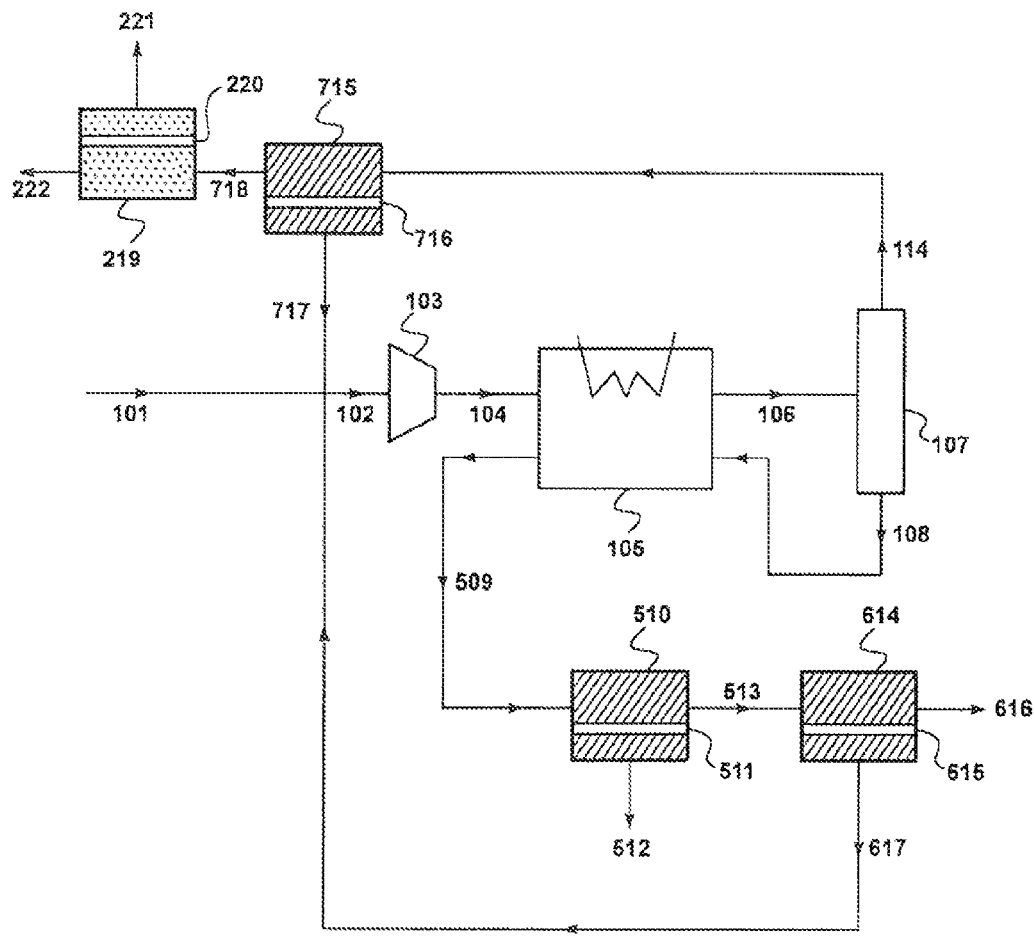
FIG. 7 is a schematic drawing showing a process flow scheme for a variant of the process of FIG. 6, in which the membrane of the second separation step is of a different material than that of the membrane in the second separation step in FIG. 6.

A basic embodiment of the purge stream recovery process is shown in FIG. 7. This embodiment is similar to that of FIG. 6, but uncondensed gas stream 114 is treated with a different membrane material.

Uncondensed gas stream, 114, is sent as a feed stream to membrane separation step, 715. This step is carried out in a membrane unit containing membranes, 716, that are selectively permeable to olefins over paraffins. Preferred membranes are similar to those used in membrane separation steps 510 and 614.

Stream 114 flows across the feed side of membrane 716. A residue stream, 718, that is depleted in olefin relative to stream 114, is withdrawn from the feed side of the membrane and sent to membrane separation step 219 for further treatment. The permeate stream, 717, is enriched in olefin, and recycled and combined with purge stream 101 upstream of compression step 103.

Figure 8:
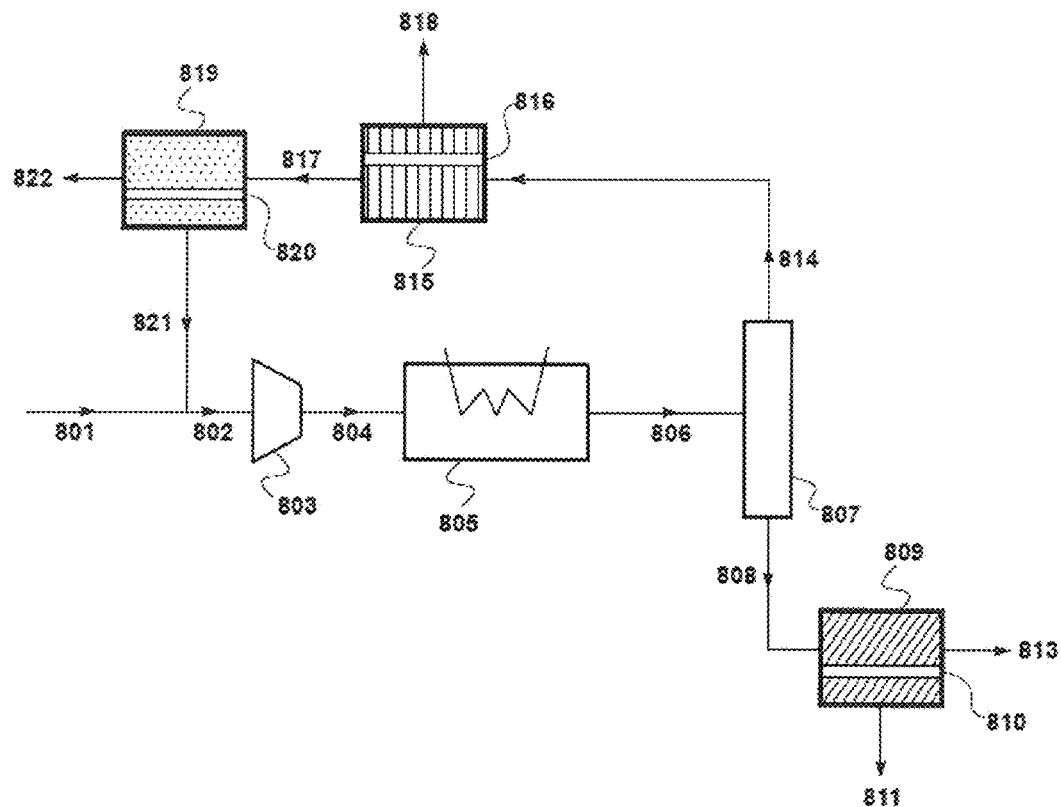
FIG. 8 is a schematic drawing showing a purge stream recovery process comprising three membrane separation steps according to a basic embodiment of the invention.

Another embodiment of the olefin, recovery process is shown in FIG. 8. This embodiment is useful when the purge stream contains hydrogen, and it is desired to recover some high purity hydrogen from this stream, rather than losing it into the residue stream of step 115.

A feed gas stream, 801, is combined with $C_{2+}$ hydrocarbon-enriched permeate stream, 821 to produce gas mixture stream 802. Gas stream 801 typically contains at least an unreacted olefin monomer and a paraffin. In this case, gas stream 801 also contains hydrogen.

Gas mixture stream 802 is routed to compression step, 803, the goal of which is to compress the stream to a pressure which the gas mixture may be partially condensed in the subsequent process steps. The compression step may be carried out using compression equipment of any convenient type, and may be performed in one stage or in a multistage compression train, depending on the degree of compression needed. It is preferred that the pressure to which stream 102 is raised be no more than about 35 bara, and more preferably no more than about 30 bara.

The stream emerging from compression step 803 is compressed stream 804. This stream is sent to a condensation step, 805. The condensation step includes cooling of stream 804 to below the olefin dewpoint temperature, such that a major portion of the olefin is condensed, followed by separation of the resulting liquid and gas phases. Cooling may be performed in any manner, and in one or more sub-steps, including, but not limited to, simple air or water aftercooling of the compressor outlet gases, heat exchange against other on-site process streams, chilling by external refrigerants, and any combinations of these. Preferably, this step should cool stream 804 to a temperature no lower than −40° C., and yet more preferably to no colder than about −35° C.

The liquid and gas phases that are formed by compression and cooling are separated by conventional means in a knockout drum or the like, 807, to yield condensed liquid stream, 808, and uncondensed gas stream, 814. The condensed liquid stream 808 typically comprises 80 mol %, 90 mol %, or more olefin and paraffin.

Stream 808 is then sent as a feed stream to a membrane separation step, 809. Any membrane with suitable performance properties may be used in this step. The membrane may take the form of a homogeneous film, an integral asymmetric membrane, a multilayer composite membrane, a membrane incorporating a gel or a liquid layer or particulates, or any other form known in the art.

The membrane or membranes to be used in step 809 are made of any material suitable for selectively permeating olefin over paraffin. Preferably, the membranes provide propylene/propane selectivity of at least 5 and propylene flux of 400 gpu under favorable conditions. For ethylene/ethane separation, the preferred selectivity of the membrane is 5 and the preferred ethylene flux is 400 gpu.

These membranes are preferably inorganic membranes. Inorganic, membranes with olefin/paraffin separating properties are very finely porous and act as very fine sieves that separate on the basis of polarity difference. Inorganic membranes are characterized by good temperature and chemical resistance. More preferably, the inorganic membranes are zeolite membranes. Such membranes include, but are not limited to zeolite-based membranes that are crystalline oxides consisting of silicon, aluminum, and other cations, such as sodium and potassium coated on ceramic or other types of support structures.

The membrane separation step, 809, may occur under vapor permeation or pervaporation conditions. By "pervaporation conditions" we mean that the feed is heated to elevate its vapor pressure but maintained at a sufficiently high pressure to prevent evaporation on the feed side of the membrane. The permeate side is maintained at a pressure substantially below the vapor pressure of the feed so vapor will permeate the membrane. If membrane separation step 809 occurs under pervaporation conditions, liquid stream 808 is first heated and then flows to and across the feed side of membrane 810. The low pressure permeate vapor, enriched in the more permeable component, may optionally be cooled and condensed (not shown) or may be compressed and condensed or a combination of the two.

If membrane separation step 809 occurs under vapor permeation conditions, liquid stream 808 is heated and vaporized (not shown) before flowing across the feed side of membrane 810.

Under either condition, a residue stream, 813, that is depleted in olefin relative to stream 808, is withdrawn from the feed side of the membrane. The membrane separation step reduces the olefin content of this stream, preferably to the point that the ratio of olefin to paraffin in the stream is reduced to about 1:1, and more preferably below 1:1. This stream may be purged from the process with comparatively little loss of olefin.

The permeate stream, 811, is enriched in olefin compared with the membrane feed. Optionally, in certain embodiments, this stream may be used as a coolant for heat recovery at various locations within the process to minimize refrigerant energy usage. For example, permeate stream 811 may be used as a coolant in the heat-exchange/condensation step 805, emerging as warmed permeate stream.

Alternatively, if membrane separation step 809 takes place under pervaporation conditions, it may be more beneficial to cool and condense stream 811 to provide or augment the driving force for the pervaporation step.

Permeate stream 811 represents a substantial source of recovered olefin, preferably containing a chemical grade olefin, having an olefin content of at least 90%.

Uncondensed gas stream, 814, is sent as a feed stream to a second membrane separation step, 815. Prior to this, it may be desirable to heat stream 814 to recover heat and/or to have optimal operating temperatures. Heating of stream 814 may be accomplished by in any way, for example by heat exchange against other on-site process stream or with steam. In FIG. 8, the heat exchange may occur between hot compressed gas stream 804 and cold uncondensed gas stream 814.

The second membrane separation step, 815, is carried out in a membrane unit containing membrane(s), 816, that are selectively permeable to hydrogen over $C_{2+}$ hydrocarbons. The membranes preferably have a selectivity for hydrogen over $C_{2+}$ hydrocarbons and other gases of at least about 10, more preferably greater than 30, and a hydrocarbon permeance of at least about 200 gpu.

Any membrane with suitable performance properties may be used in the second membrane separation step, 815. The membrane may take the form of a homogeneous film, an integral asymmetric membrane, a multilayer composite membrane, a membrane incorporating a gel or liquid layer or particulates, or any other form known in the art.

Representative preferred polymeric membranes have a selective based on a polyimide or a polyimide derivative. Other polymeric materials suitable for the selective layer include polybenzimidazole and its derivatives, and polybenzoxazole. Representative materials suitable for inorganic membranes include metals, metal alloys, and ceramics of various types. Yet other suitable membranes include dense ion-transport membranes or proton-conducting membranes.

A driving force for transmembrane permeation is provided by a pressure difference between the feed and permeate sides of the membrane. If the uncondensed gas after the condensation step remains at high pressure, such as above 5 bara, than this is usually adequate to carry out the membrane separation step without additional compression.

Stream 814 flows across the feed side of membrane 816. A residue stream, 817, that is depleted in hydrogen relative to stream 814, is withdrawn from the feed side of the membrane. The permeate stream, 818, is enriched in hydrogen compared with the membrane feed. Preferably this stream contains 80 mol % or more of hydrogen, and can be a useful source of hydrogen.

Residue stream, 817, depleted in hydrogen compared to stream 814 is further treated by membrane separation step 819. Residue stream 817 is passed as a feed stream across membrane 820 that is selectively permeable to $C_{2+}$ hydrocarbons over other gases. Preferably, these membranes are the same as those used in membrane separation step 115 of FIG. 1. The residue stream, 822, contains waste gases, such as nitrogen or methane. The permeate stream, 821, is enriched in $C_{2+}$ hydrocarbons and is recycled upstream of compression step 803.

The invention is now further described by the following examples, which are intended to be illustrative of the invention, but are not intended to limit the scope or underlying principles in any way.

EXAMPLES

Example 1

Treatment of the Uncondensed Gas Stream Not in Accordance with the Invention

For comparison with the following examples, a calculation was performed in a process where only the uncondensed gas stream 114 from separator 107 was treated. In other words, stream 108 was withdrawn from the separator and was not further treated. The treatment included using two membrane separation steps, similar to steps 115 and 219 in FIG. 2. Likewise, the streams are labeled to correspond with the treatment process of the uncondensed gas stream represented in FIG. 2.

For the calculation, the purge stream was assumed to have a flow rate of 1,139 kg/hour and contain propylene, propane, and nitrogen. It as also assumed that the molar compositions were approximately as follows:

Nitrogen: 76%
Propylene: 21%
Propane: 3%

It was further assumed that the purge stream was compressed to 24 bara in compression step 103, then cooled to −20° C. in condensation step 105.

The calculation was performed using differential element membrane code written at MTR and incorporated into a computer process simulation program (ChemCad 6.3, ChemStations, Austin, Tex.).

The results of the calculations are shown in Table 1:

TABLE 1

| Stream | 101 | 102 | 104 | 106 | 108 | 114 | 117 | 118 | 221 | 222 |
|---|---|---|---|---|---|---|---|---|---|---|
| Total Mass flow (kg/h) | 1,139 | 2,642 | 2,642 | 2,642 | 367 | 2,275 | 1,503 | 772 | 135 | 637 |
| Temp (° C.) | 70 | 46 | 90 | −20 | −20 | −20 | 28 | 22 | 22 | 21 |
| Pressure (bara) | 1 | 1 | 24 | 23 | 23 | 23 | 1 | 23 | 3 | 23 |
| Component (mol %) | | | | | | | | | | |
| Nitrogen | 75.9 | 74.6 | 74.6 | 74.6 | 3.7 | 83.0 | 73.7 | 99.0 | 96.9 | 99.5 |
| Propylene | 20.8 | 22.1 | 22.1 | 22.1 | 83.1 | 15.0 | 23.1 | 0.8 | 2.7 | 0.5 |
| Propane | 3.3 | 3.2 | 3.2 | 3.2 | 13.2 | 2.1 | 3.2 | 0.1 | 0.4 | 0.1 |
| Mass flow (kg/h) | | | | | | | | | | |
| Nitrogen | 770 | 1,746 | 1,746 | 1,746 | 9 | 1,737 | 976 | 761 | 129 | 632 |
| Propylene | 317 | 770 | 777 | 777 | 307 | 470 | 461 | 10 | 5 | 4 |
| Propane | 52 | 119 | 119 | 119 | 51 | 68 | 66 | 1 | 1 | 1 |

With only uncondensed gas stream 114 being treated, the process recovers about 640 kg/h of 99.5% purity nitrogen for reuse in the purge bin. No olefin depleted in paraffin is recovered.

Example 2

Purge Stream Recovery Process in Accordance with the Invention of FIG. 3

A calculation was performed to model the performance of the process of FIG. 3 in treating a purge stream from a purge bin offgas of a polymerization process. The membrane separation of the liquid condensate occurred under pervaporation conditions.

The results of the calculations are shown in Table 2.

TABLE 2

| Stream | 101 | 108a | 108b | 111 | 113 | 316 | 317 | 114 | 117 | 118 | 221 | 222 |
|---|---|---|---|---|---|---|---|---|---|---|---|---|
| Mass flow (kg/h) | 1,139 | 805 | 805 | 325 | 480 | 43 | 437 | 2,270 | 1,500 | 771 | 135 | 636 |
| Temp (° C.) | 70 | −20 | 40 | 40 | 40 | 38 | 29 | −20 | 28 | 22 | 22 | 21 |
| Pressure (bara) | 1 | 23 | 23 | 1 | 22 | 21 | 1 | 23 | 1 | 23 | 3 | 23 |
| Component (mol %) | | | | | | | | | | | | |
| Nitrogen | 75.9 | 3.8 | 3.8 | 0.5 | 6.0 | 30.0 | 3.4 | 83.2 | 61.2 | 99.0 | 97.0 | 99.5 |
| Propylene | 20.8 | 76.5 | 76.5 | 93.8 | 64.9 | 7.1 | 71.1 | 13.8 | 30.3 | 0.8 | 2.5 | 0.4 |
| Propane | 3.3 | 19.8 | 19.8 | 5.8 | 29.1 | 62.9 | 25.5 | 3.1 | 8.5 | 0.2 | 0.6 | 0.1 |
| Mass flow (kg/h) | | | | | | | | | | | | |
| Nitrogen | 770 | 20 | 20 | 1 | 19 | 9 | 10 | 1,737 | 977 | 760 | 129 | 631 |
| Propylene | 316 | 618 | 618 | 304 | 313 | 3 | 310 | 432 | 424 | 9 | 5 | 4 |
| Propane | 53 | 167 | 167 | 20 | 148 | 31 | 117 | 101 | 99 | 2 | 1 | 1 |

Using polymeric membranes to treat the uncondensed gas stream and inorganic membranes to treat the condensate, the process achieves 96% recovery of olefin. The ratio of olefin to paraffin in purge stream 316 is reduced to about 1:10.

Example 3

Purge Stream Recovery Process in Accordance with the Invention of FIG. 5

A calculation was performed to model the performance of the process of FIG. 5 in treating a purge stream from a polyolefin manufacturing process. The results of the calculations are shown in Table 3.

TABLE 3

| Stream | 101 | 108 | 509 | 512 | 513 | 114 | 117 | 118 | 221 | 222 |
|---|---|---|---|---|---|---|---|---|---|---|
| Mass flow ((kg/h) | 1,139 | 367 | 367 | 300 | 68 | 2,275 | 1,503 | 772 | 135 | 637 |
| Temp (° C.) | 70 | −20 | 33 | 31 | 29 | −20 | 28 | 22 | 22 | 21 |
| Pressure (barn) | 1 | 23 | 3 | 1 | 3 | 23 | 1 | 23 | 3 | 23 |
| Component (mol %) | | | | | | | | | | |
| Nitrogen | 75.9 | 3.7 | 3.7 | 0.8 | 16.2 | 83.0 | 73.7 | 99.0 | 96.9 | 99.5 |
| Propylene | 20.8 | 83.1 | 83.1 | 92.9 | 41.0 | 15.0 | 23.1 | 0.8 | 2.7 | 0.4 |
| Propane | 3.3 | 13.2 | 13.2 | 6.2 | 42.8 | 2.1 | 3.2 | 0.1 | 0.4 | 0.1 |
| Mass flow (kg/h) | | | | | | | | | | |
| Nitrogen | 770 | 9 | 9 | 2 | 8 | 1,737 | 976 | 761 | 129 | 632 |
| Propylene | 317 | 307 | 307 | 278 | 29 | 470 | 461 | 10 | 5 | 4 |
| Propane | 52 | 51 | 51 | 20 | 31 | 68 | 66 | 1 | 1 | 1 |

Using polymeric membranes to treat the uncondensed gas stream and an inorganic membrane to treat the condensate, the process achieves 88% recovery of olefin. The ratio of propylene to propane in purge stream 513 is reduced to less than 1:1.

Example 4

Purge Stream Recovery Process in Accordance with the Invention of FIG. 6

A calculation was performed to model the performance of the process of FIG. 6 in treating a purge stream from a polyolefin manufacturing process. The results of the calculations are shown in Table 4

Using polymeric membranes to treat the uncondensed gas stream and inorganic membranes to treat the condensate, the process achieves 96% recovery of olefin. The ratio of olefin to paraffin in purge stream 616 is reduced to about 1:10.

Example 5

Purge Stream Recovery Process in Accordance with the Invention of FIG. 7

A calculation was performed to model the performance of the process of FIG. 7 in treating a purge stream from a polyolefin manufacturing process. The results of the calculations are shown in Table 5,

TABLE 4

| Stream | 101 | 108 | 509 | 512 | 513 | 616 | 617 | 114 | 117 | 118 | 221 | 222 |
|---|---|---|---|---|---|---|---|---|---|---|---|---|
| Mass flow (kg/h) | 1,139 | 805 | 805 | 325 | 480 | 43 | 437 | 2,270 | 1,500 | 771 | 135 | 636 |
| Temp (° C.) | 70 | −20 | 33 | 32 | 32 | 27 | 29 | −20 | 28 | 22 | 22 | 21 |
| Pressure (bara) | 1 | 23 | 3 | 1 | 3 | 3 | 1 | 23 | 1 | 23 | 3 | 23 |
| Component (mol %) | | | | | | | | | | | | |
| Nitrogen | 75.9 | 3.8 | 3.8 | 0.5 | 6.0 | 30.0 | 3.4 | 83.2 | 61.2 | 99.0 | 97.0 | 99.5 |
| Propylene | 20.8 | 76.5 | 76.5 | 93.8 | 64.9 | 7.1 | 71.1 | 13.8 | 30.3 | 0.8 | 2.5 | 0.4 |
| Propane | 3.3 | 19.8 | 19.8 | 5.8 | 29.1 | 62.9 | 25.5 | 3.1 | 8.5 | 0.2 | 0.6 | 0.1 |
| Mass flow (kg/h) | | | | | | | | | | | | |
| Nitrogen | 770 | 1 | 20 | 1 | 19 | 9 | 10 | 1,737 | 977 | 760 | 129 | 631 |
| Propylene | 316 | 618 | 618 | 304 | 313 | 3 | 310 | 432 | 424 | 9 | 5 | 4 |
| Propane | 53 | 167 | 167 | 20 | 148 | 31 | 117 | 101 | 99 | 2 | 1 | 1 |

TABLE 5

| Stream | 101 | 108 | 509 | 512 | 5 | 616 | 617 | 114 | 717 | 718 | 221 | 222 |
|---|---|---|---|---|---|---|---|---|---|---|---|---|
| Mass flow (kg/h) | 1,142 | 751 | 751 | 329 | 421 | 21 | 400 | 1,383 | 591 | 791 | 219 | 572 |
| Temp (° C.) | 70 | −20 | 33 | 32 | 32 | 27 | 29 | −20 | 29 | 26 | 24 | 24 |
| Pressure (bara) | 1 | 23 | 3 | 1 | 3 | 3 | 1 | 23 | 1 | 23 | 3 | 23 |
| Component (mol %) | | | | | | | | | | | | |
| Nitrogen | 75.9 | 3.8 | 3.8 | 0.5 | 6.3 | 39.3 | 4.4 | 83.1 | 40.5 | 97.7 | 93.9 | 99.1 |
| Propylene | 20.8 | 77.6 | 77.6 | 94.0 | 64.9 | 3.5 | 68.6 | 14.0 | 47.3 | 0.2 | 0.7 | 0.1 |
| Propane | 3.3 | 18.6 | 18.6 | 5.5 | 28.8 | 57.2 | 27.1 | 2.9 | 12.2 | 2.1 | 5.5 | 0.8 |
| Mass flow (kg/h) | | | | | | | | | | | | |
| Nitrogen | 770 | 19 | 19 | 1 | 18 | 6 | 12 | 1,058 | 295 | 763 | 199 | 564 |
| Propylene | 313 | 585 | 585 | 309 | 275 | 1 | 274 | 267 | 264 | 3 | 2 | 1 |
| Propane | 59 | 147 | 147 | 19 | 128 | 14 | 114 | 58 | 32 | 25 | 18 | 7 |

Using the combination of a polymeric membrane and an inorganic membrane to treat the uncondensed gas stream and inorganic membranes to treat the condensate, the process achieves almost 99% recovery of olefin at 94% purity. The ratio of olefin to paraffin in purge stream 616 is reduced to 1:14.

Example 6

Purge Stream Recovery Process in Accordance with the Invention of FIG. 7

A calculation was performed to model the performance of the process of FIG. 7 in treating a purge stream from a polyolefin manufacturing process. All assumptions regarding stream composition and operating conditions were the same as in Example 5 unless otherwise stated. Recycle rates, membrane operating pressures and membrane areas are selected to recover propylene at a higher purity than previous examples.

TABLE 6

| Stream | 101 | 108 | 509 | 512 | 513 | 616 | 617 | 114 | 717 | 718 | 221 | 222 |
|---|---|---|---|---|---|---|---|---|---|---|---|---|
| Mass flow (kg/h) | 1,142 | 4,670 | 4,670 | 236 | 4,434 | 210 | 4,224 | 1,286 | 605 | 682 | 201 | 480 |
| Temp (° C.) | 70 | −20 | 50 | 50 | 50 | 40 | 40 | −20 | 29 | 25 | 24 | 23 |
| Pressure (bara) | 1 | 23 | 23 | 3 | 23 | 23 | 4 | 23 | 1 | 23 | 3 | 23 |
| Component (mol %) | | | | | | | | | | | | |
| Nitrogen | 75.9 | 3.6 | 3.6 | 0.2 | 3.8 | 54.3 | 0.8 | 82.7 | 59.9 | 99.6 | 99.0 | 99.9 |
| Propylene | 20.8 | 94.6 | 94.6 | 99.6 | 94.3 | 27.1 | 98.4 | 17.0 | 39.7 | 0.2 | 0.5 | 0.1 |
| Propane | 3.3 | 1.8 | 1.8 | 0.2 | 1.9 | 18.5 | 0.8 | 0.3 | 0.4 | 0.2 | 0.5 | 0.1 |
| Mass flow (kg/h) | | | | | | | | | | | | |
| Nitrogen | 770 | 115 | 115 | 1 | 115 | 92 | 22 | 979 | 301 | 678 | 198 | 479 |
| Propylene | 313 | 4,468 | 4,468 | 235 | 4,233 | 69 | 4,164 | 302 | 300 | 2 | 1 | 1 |
| Propane | 59 | 88 | 88 | 1 | 87 | 49 | 38 | 5 | 3 | 2 | 2 | 1 |

Using the combination of a polymeric membrane and an inorganic membrane to treat the uncondensed gas stream and inorganic membranes to treat the condensate, the process achieves 75% recovery of olefin at 99.6% purity. The ratio of olefin to paraffin in purge stream 616 is reduced to 1:0.7.

Example 7

Figure 9:
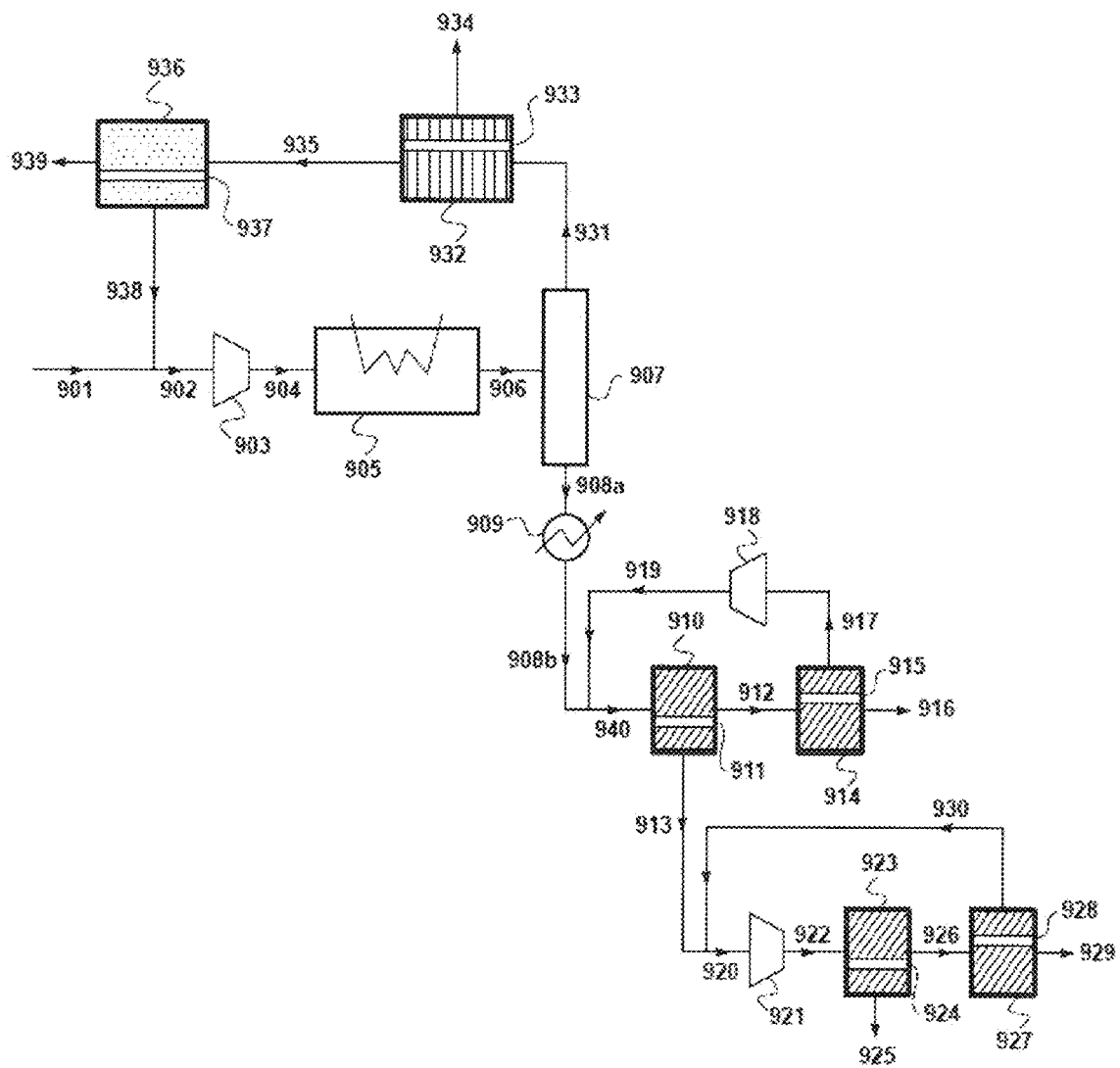
FIG. 9 is a schematic drawing showing a process of a variant of process of FIG. 9, comprising a series of inorganic membranes arranged as multi-stage, multi-step units to treat the condensate stream in order to obtain a high olefin recovery.

Purge Stream Recovery Process in Accordance with the Invention of FIG. 9

A calculation was performed to model a process in which the purge stream contains hydrogen. For the calculation, the purge stream was assumed to have a flow rate of 22,000 kg/hour and contain propylene, propane, hydrogen, nitrogen, methane, ethylene, and ethane. It was also assumed that the molar compositions were approximately as follows:
Propane: 38%
Hydrogen: 30%
Propylene: 26%
Methane: 3%
Nitrogen: 1%
Ethylene: 1%
Ethane: 1%

It was further assumed that the purge stream was compressed to 24 bara in compression step 903, then cooled to −20° C. in condensation step 905.

The calculation was performed using differential element membrane code written at MTR and incorporated into a computer process simulation program (ChemCad ChemStations, Austin, Tex.).

Referring to FIG. 9, a purge stream, 901, is combined with a $C_{2+}$ hydrocarbon-enriched permeate stream, 938, to produce a gas mixture stream, 902. Gas mixture stream 902 is routed to a compression step, 903. The stream emerging from compression step 903 is a compressed stream, 904.

Compressed stream 904 is directed to a condensation step 905. The condensation step includes cooling of stream 904 to below the olefin dewpoint temperature, such that a major portion of the olefin is condensed, followed by separation of the resulting liquid and gas phases. The liquid and gas phases that are formed by compression and cooling are separated by conventional means in a knock-out drum or the like, 907, to yield a condensed liquid stream, 908a, and an uncondensed gas stream, 931.

Condensed liquid stream 908a is heated by direct heater, 909, of any convenient type to produce a vapor stream 908b. In the alternative, stream 908a could be vaporized using a lower temperature heat source by reducing the pressure on the stream by means of a valve or the like. In some embodiments, the cold condensed liquid stream 908a may be heated by heat exchange with the hot compressed gas stream, 904.

Vapor stream 908b is then mixed with a second compressed stream 919 to produce a second mixed gas stream, 940. Second mixed gas stream 940 is passed as a feed stream to a first membrane separation step, 910. Membrane or membranes, 911, to be used in step 910 are inorganic membranes, but any other material suitable for selectively permeating olefin over paraffin may be used. A first residue stream, 912, that is depleted in olefin relative to stream 940, is withdrawn from the feed side of membrane 911. A first permeate stream, 913, enriched in olefin compared to stream 940, is withdrawn from the permeate side of the membrane.

First residue stream 912 undergoes further separation by being passed as a feed stream to a second membrane separation step, 914. The membrane or membranes, 915, to be used in step 914 are inorganic membranes, like those used in step 910. A second residue stream, 916, that is depleted in olefin relative to stream 914, is withdrawn from the feed side of the membrane. This stream may be purged from the process with comparatively little loss of olefin. A second permeate stream, 917, enriched in olefin compared to stream 912, is withdrawn from the permeate side of the membrane. This stream recycled by being sent to compressor 919 and mixed with stream 908h to produce second mixed gas stream 940.

First permeate stream 913 is combined with fourth permeate stream 930 to produce third mixed gas stream 920. Third mixed gas stream 920 is compressed by compressor 921 to form a third compressed stream, 922.

Compressed stream 922 is then treated by a third membrane separation step, 923. Similar to the membrane separation steps above, the membrane or membranes, 924, to be used in step 923 are inorganic membranes. A third residue stream, 926, that is depleted in olefin relative to stream 922, is withdrawn from the feed side of the membrane. Third permeate stream 925 is enriched in olefin compared with the membrane feed and may be recycled hack to the polymerization reactor or sent for further processing.

Third residue stream 926 is passed as a feed stream to a fourth membrane separation step, 927. The membrane or membranes to be used in step 927 are inorganic membranes, like the previous steps. A fourth residue stream, 929, that is depleted in olefin relative to stream 926, is withdrawn from the feed side of membrane 928. This stream may be purged from the process with comparatively little loss of olefin. A fourth permeate stream, 930, enriched in olefin compared to stream 926, is withdrawn from the permeate side of the membrane and recycled back to the process prior to third compressor 921.

Membrane separation steps 914 and 927 reduce the olefin content of this stream, preferably to the point that the ratio of olefin to paraffin in the stream is reduced to about 1:1, and more preferably below 1:1.

Uncondensed gas stream, 931, is sent as a feed stream to a fifth membrane separation step, 932. Prior to this, it may be desirable to heat stream 931 (not shown) to recover heat and/or to have optimal operating temperatures. Heating of stream 931 may be accomplished by in any way, for example by heat exchange against other on-site process stream or with steam.

Fifth membrane separation step 932 is carried out in a membrane unit containing membrane(s), 933, that are selectively permeable to hydrogen over $C_{2+}$ hydrocarbons and other gases. The material making up the membrane is the same material as membrane 816, discussed above.

Uncondensed gas stream 931 flows across the feed side of membrane 933. A fifth residue stream, 935, that is depleted in hydrogen relative to stream 931, is withdrawn from the feed side of the membrane. A fifth permeate stream, 934, is enriched in hydrogen compared with the membrane feed.

Fifth residue stream, 935, depleted in hydrogen compared to stream 931 is further treated by a sixth membrane separation step, 936. Fifth residue stream 935 is passed as a feed stream across membrane 937, which is selectively permeable to $C_{2+}$ hydrocarbons over other gases. These membranes are the same as those used in membrane separation step 115 of FIG. 1. The sixth residue stream, 939, contains waste gases, such as nitrogen or methane. The sixth permeate stream, 938, is enriched in hydrocarbons and is recycled upstream of first compression step 903.

The results of the calculations are shown in Table 7:

TABLE 7

| Stream | 901 | 902 | 906 | 909b | 940 | 912 | 917 | 916 | 913 | 920 |
|---|---|---|---|---|---|---|---|---|---|---|
| Mass flow (kg/h) | 22,000 | 27,163 | 27,163 | 21,277 | 46,367 | 36,891 | 25,090 | 11,801 | 9,476 | 42,120 |
| Temp (° C.) | 40 | 38 | 40 | 100 | 100 | 96 | 85 | 74 | 98 | 81 |
| Pressure (bara) | 10 | 10 | 24 | 24 | 24 | 2 | 24 | 2 | 2 | 2 |
| Component (mole %) | | | | | | | | | | |
| Nitrogen | 1.0 | 3.1 | 3.1 | 0.3 | 0.1 | 0.2 | 0.0 | 0.5 | 0.0 | 0.0 |
| Hydrogen | 30.0 | 29.3 | 29.3 | 1.3 | 0.7 | 0.9 | 0.2 | 2.3 | 0.0 | 0.0 |
| Methane | 3.0 | 10.2 | 10.2 | 3.5 | 2.3 | 2.8 | 1.2 | 6.1 | 0.3 | 0.1 |
| Ethylene | 1.0 | 1.4 | 1.4 | 1.4 | 2.2 | 2.0 | 2.9 | 0.3 | 2.8 | 3.9 |
| Ethane | 1.0 | 1.2 | 1.2 | 1.4 | 1.9 | 2.1 | 2.3 | 1.8 | 1.0 | 0.6 |
| Propylene | 26.01 | 22.6 | 22.6 | 37.3 | 45.1 | 35.4 | 51.8 | 1.2 | 83.2 | 90.3 |
| Propane | 38.01 | 32.3 | 32.3 | 54.7 | 47.6 | 56.6 | 41.5 | 87.9 | 12.7 | 5.1 |
| Flow rates (kg/h) | | | | | | | | | | |
| Nitrogen | 208 | 851 | 851 | 43 | 46 | 46 | 3 | 42 | 0 | 0 |
| Hydrogen | 449 | 581 | 581 | 13 | 16 | 16 | 3 | 13 | 0 | 0 |
| Methane | 357 | 1,610 | 1,610 | 293 | 412 | 400 | 119 | 281 | 11 | 15 |
| Ethylene | 208 | 381 | 381 | 199 | 682 | 504 | 483 | 21 | 179 | 1,096 |

TABLE 7-continued

| | | | | | | | | | |
|---|---|---|---|---|---|---|---|---|---|
| Ethane | 723 | 350 | 350 | 221 | 632 | 567 | 412 | 155 | 66 | 193 |
| Propylene | 8,120 | 9,378 | 9,378 | 8,090 | 21,174 | 13,226 | 13,084 | 141 | 7,948 | 38,535 |
| Propane | 12,435 | 14,012 | 14,012 | 12,419 | 23,405 | 22,133 | 10,986 | 11,147 | 1,272 | 2,280 |

| Stream | 926 | 930 | 929 | 925 | 931 | 934 | 935 | 938 | 939 |
|---|---|---|---|---|---|---|---|---|---|
| Mass flow (kg/h) | 34,145 | 32.644 | 1,501 | 7,975 | 5,886 | 519 | 5,367 | 5,163 | 204 |
| Temp (° C.) | 96 | 76 | 56 | 98 | 35 | 35 | 38 | 32 | 26 |
| Pressure (bara) | 24 | 2 | 24 | 2 | 24 | 1 | 23 | 10 | 23 |
| Component (mole %) | | | | | | | | | |
| Nitrogen | 0.0 | 0.0 | 0 0 | 0.0 | 61 | 05 | 10.9 | 9.5 | 39.4 |
| Hydrogen | 0.0 | 0.0 | 0.3 | 0.0 | 59.9 | 98.3 | 27.4 | 27.1 | 35.2 |
| Methane | 0.1 | 0.0 | 2.0 | 0.0 | 17.5 | 0.7 | 31.6 | 32.2 | 20.4 |
| Ethylene | 4.1 | 4.2 | 3.5 | 2.7 | 14 | 0.1 | 2.4 | 2.5 | 0.6 |
| Ethane | 0.7 | 0.5 | 5.2 | 0.2 | 0.9 | 0.0 | 1.7 | 1.7 | 0.4 |
| Propylene | 88.9 | 92.4 | 12.0 | 96.5 | 6.5 | 0.2 | 11.8 | 12.3 | 1.8 |
| Propane | 6.1 | 2.9 | 77.0 | 0.7 | 7.7 | 0.1 | 14.1 | 14.7 | 2.2 |
| Flow rates (kg/h) | | | | | | | | | |
| Nitrogen | 0 | 0 | 0 | 0 | 809 | 33 | 776 | 643 | 132 |
| Hydrogen | 0 | 0 | 0 | 0 | 568 | 427 | 141 | 132 | 8 |
| Methane | 15 | 4 | 11 | 0 | 1,317 | 25 | 1,292 | 1,253 | 39 |
| Ethylene | 953 | 918 | 35 | 143 | 182 | 7 | 175 | 173 | 2 |
| Ethane | 184 | 128 | 56 | 9 | 130 | 1 | 129 | 127 | 2 |
| Propylene | 30,768 | 30,587 | 181 | 7,767 | 1,288 | 21 | 1,267 | 1,258 | 9 |
| Propane | 2,225 | 1,008 | 1,217 | 55 | 1,593 | 5 | 1,588 | 1,576 | 11 |

Using a hydrogen-selective membrane in combination with a polymeric membrane to treat the uncondensed gas stream and a series of inorganic membranes to treat the condensate, the process achieves 96% recovery of olefin at 97% purity. The ratio of olefin to paraffin in purge streams 916 and 929 is reduced to 1:79 and 1:7, respectively.

I claim:

1. A process for treating a purge stream from a polymer manufacturing operation, said purge stream comprising at least an olefin, a paraffin, and hydrogen, comprising the steps of:
   (a) passing the feed gas stream to a compressor to produce a compressed stream;
   (b) partially condensing the compressed stream, including cooling and separating the compressed stream into a condensed liquid condensate enriched in olefin and paraffin and an uncondensed (residual) gas stream depleted in olefin and paraffin relative to the compressed stream;
   (c) separating the condensed liquid condensate from step (b) using a first membrane to produce a first olefin-enriched permeate stream and a first paraffin-enriched residue stream;
   (d) separating the uncondensed gas stream from step (b) using a second membrane to produce a hydrogen-enriched permeate stream and a hydrogen-depleted residue stream;
   (e) separating the hydrogen-depleted residue from step (d) using a third membrane to produce a hydrocarbon-enriched permeate stream and a hydrocarbon-depleted residue stream; and
   (f) returning the hydrocarbon-enriched permeate stream upstream of the compressor.

2. The process of claim 1, wherein the olefin is ethylene.
3. The process of claim 1, wherein the olefin is propylene.
4. The process of claim 1, wherein the olefin is butylene.
5. The process of claim 1, wherein the first membrane is an inorganic membrane.
6. The process of claim 1, wherein the second membrane is a polymeric membrane.
7. The process of claim 1, wherein the third membrane is a polymeric membrane.

8. The process of claim 1, further comprising the steps of:
   (g) separating the first paraffin-enriched residue stream using a fourth membrane to produce a second olefin-enriched permeate stream and a second paraffin-enriched residue stream; and
   (h) returning the second olefin-enriched permeate stream upstream of the compressor.

9. The process of claim 8, wherein the fourth membrane is an inorganic membrane.

10. A process for treating a purge stream from a polymer manufacturing operation, said purge stream comprising at least an olefin, a paraffin, and hydrogen, comprising the steps of:
    (a) passing said gas stream to a compressor to produce a compressed stream;
    (b) partially condensing the compressed stream, including cooling and separating the compressed stream into a condensed liquid stream enriched in olefin and paraffin and an overhead gas stream depleted in olefin and paraffin;
    (c) vaporizing the condensed liquid stream to create a vapor feed stream;
    (d) separating the vapor feed stream from step (c) using a first membrane to produce a first olefin-enriched permeate stream and a first paraffin-enriched residue stream;
    (e) separating the overhead gas stream from step (b) using a second membrane to produce a hydrogen-enriched permeate stream and a hydrocarbon-depleted residue stream;
    (f) separating the hydrogen-depleted residue stream from step (e) using a third membrane to produce a hydrocarbon-enriched permeate stream and a hydrocarbon-depleted residue stream; and
    (g) returning the hydrocarbon-enriched permeate stream upstream of the compressor.

11. The process of claim 10, wherein the first membrane is an inorganic membrane.
12. The process of claim 10, wherein the second membrane is a polymeric membrane.
13. The process of claim 10, wherein the third membrane is a polymeric membrane.

14. The process of claim 10, further comprising the steps of:
  (h) passing the first paraffin-enriched residue stream from step (d) as a feed stream across a fourth membrane to produce a second olefin-enriched permeate stream and a second paraffin-enriched residue stream; and
  (i) returning the second olefin-enriched permeate stream ups; of the compressor.

15. The process of claim 14, wherein the fourth membrane is an inorganic membrane.

\* \* \* \* \*